Figure 1:
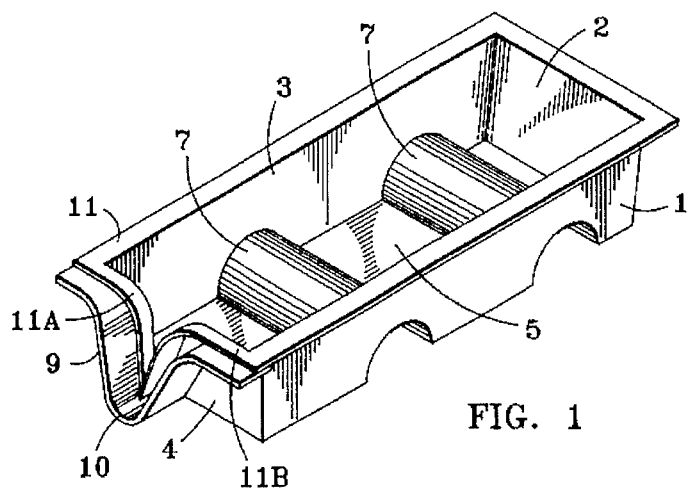

United States Patent [19]
Vargas, III

[11] Patent Number: 5,542,533
[45] Date of Patent: Aug. 6, 1996

[54] SURGICAL SCALPEL CRADLE

[76] Inventor: Joseph H. Vargas, III, 3 Albert Cree Dr., Rutland, Vt. 05701

[21] Appl. No.: 452,523

[22] Filed: May 30, 1995

[51] Int. Cl.⁶ .................................................. B65D 83/10
[52] U.S. Cl. .......................... 206/363; 206/359; 206/370; 206/564
[58] Field of Search .................................. 206/363, 366, 206/370, 359, 564

[56] References Cited

U.S. PATENT DOCUMENTS

| | | | |
|---|---|---|---|
| 4,784,267 | 11/1988 | Gessler et al. | 206/370 |
| 4,961,500 | 10/1990 | Coulombe | 206/366 |
| 4,974,728 | 12/1990 | Colton | 206/366 |
| 5,007,535 | 4/1991 | Meseke et al. | 206/366 |
| 5,275,280 | 1/1994 | Everhart | 206/370 |
| 5,368,580 | 11/1994 | Susuki | 206/366 |
| 5,407,069 | 4/1995 | Schmieding et al. | 206/370 |

*Primary Examiner*—David T. Fidei
*Attorney, Agent, or Firm*—John J. Welch, Jr. Esq.

[57] ABSTRACT

A scalpel cradle with a floor and four outwardly inclined sidewalls, with two convex elevations in the floor extending from one lateral side of the cradle to the other side of the receptor and with a rectilinear cap the anterior portion of which is in the shape of a symmetrical letter Y which is compressibly elastic in the vicinity of the leg component of the anterior portion such that the bipartite leg component of the anterior portion is amenable to receipt of the handle of a surgical scalpel resting therein on its bottom side, and with a outwardly directed curvaceous extension affixed to the anterior portion and in the shape of a downwardly directed u-shaped curve.

2 Claims, 3 Drawing Sheets

SURGICAL SCALPEL CRADLE

BACKGROUND OF THE INVENTION

1. Field of the Invention

The instant invention is one of those surgical devices that facilitates safe and effective dispensing and retrieval of scalpels during surgery.

2. Related Prior Art

The following references vaguely resemble but do not anticipate the instant invention:

| Inventor | Invention | Patent No. | Date |
| --- | --- | --- | --- |
| 1. Donahue | Surgical Scalpel Holder | 5,301,807 | 4/12/94 |
| 2. Sandel et al. | Medical Instrument Holder and Sharps Disposal Container | 5,024,326 | 6/18/91 |
| 3. Simmons | Presentation Tray for Surgical Instruments | 5,381,896 | 1/17/95 |
| 4. Baskas | Disposable Syringe Needle and Scalpel Holder | 5,102,083 | 4/7/92 |
| 5. Horan et al. | Instrument Tray with Instrument Supports | 5,339,955 | 8/23/94 |
| 6. Frauenhoffer | Surgical Blade Remover | 4,466,539 | 8/21/84 |
| 7. Lahay | Device for Organizing Objects | 3,696,920 | 10/10/72 |
| 8. W. J. Anderson III | Instrument Tray | 2,903,129 | 3/30/56 |
| 9. T F Bates | Sterilizing and Operation Instrument Tray | 2,018,651 | 11/12/34 |

A SUMMARY OF THE INVENTION

1. A Brief Description of the Invention

The instant invention is a recessed tray unit. It has a floor which is, in turn, joined to the bottom edges of each of four outwardly inclined sidewalls. The absolute values of the angles of inclination outward of all four sidewalls relative to the level portion of the floor are all roughly equal to one another. There is an anterior sidewall also joined at one end edge to the anterior edge of a first lateral sidewall as well as being joined at its other end edge to the anterior edge of a second lateral sidewall. There is a posterior sidewall joined at one end edge to the posterior edge of the invention's first lateral sidewall as well as being joined at its other edge to the posterior edge of the invention's second lateral sidewall. The floor of the invention is level in its mid-section and at and about its anterior sidewall and at and about its posterior sidewall. There are two convex shaped elevations in the floor each of which extend from the surface of the first lateral sidewall to the surface of the second lateral sidewall. One of these elevations is everywhere closer to the anterior sidewall than the other and is the anterior boundary of the floor's level midsection. The other of these elevations is everywhere closer to the posterior sidewall than the first noted elevation and is the posterior boundary of the floor's level midsection. The anterior sidewall of the invention has frontally affixed thereto, a horizontally outwardly directed curvaceous extension thereof in the shape of a vertically downwardly directed u-shaped curve, the minimum points of which lie on a horizontally inclined line an extension of which would run from the anterior sidewall to the posterior sidewall and be parallel to the line that would constitute the long horizontally inclined central axis of symmetry of the invention. Centrally positioned within the anterior sidewall is a notch. Positioned atop the top edged of the invention's four sidewalls and affixed thereto is a hollow rectilinear cap, the anterior portion of which resembles a letter Y, the arms of which each symmetrically curve inwardly and downwardly into a leg so as to centrally fit within the confines of the previously described notch. The anterior portion of the cap is compressibly elastic in the vicinity of and throughout the leg with a vertical slit cut into the leg.

As respects use of the invention, a surgical scalpel is tossed into the recessed tray unit by a surgeon. A nurse then places the handle of the scalpel into the compressible, elastic bipartite leg component of the anterior portion of the invention's rectilinear cap from where it can conveniently be later withdrawn for use handle first by the surgeon without having to look at it as he or she does so.

2. Objects of the Invention

One object of the instant invention is to markedly minimize the probability that a scalpel sought to be temporarily discarded by a surgeon during surgery might cut the hand of a surgical nurse during the process of a discarding of the scalpel. In the conventional surgical setting, a surgeon seeking to temporarily discard a scalpel, hands it out to be taken from the surgeon by a nurse. From time to time, the scalpel in such a setting can end up being handled by its blade by the nurse resulting in cuts being suffered by the nurse and occasionally concomitant infection if the blood on the scalpel should, by chance, be contaminated. Obviously, in view of the scourge of AIDS as well as that of hepatitis so prevalent today, such a prospect for infection is a matter of no small concern to surgical nurses working in such a setting.

The instant invention serves to virtually obliterate such concerns on the part of surgical nurses. With resort to utilization of the instant invention, when a surgeon seeks to temporarily discard a scalpel, during surgery, instead of handing it to a nurse, the surgeon simply drops the scalpel into the well of the instant invention from where it can then be repositioned therein and between the compressibly elastic halves of the slit leg of the anterior portion of the invention's rectilinear cap by a nurse for eventual reuse by the surgeon without anyone ever touching the scalpel's blade.

Another object of the instant invention is to markedly minimize the need for a surgeon's eyes to stray from the surgical field into which they are focused at a time when the surgeon seeks to discard a scalpel or retrieve a scalpel previously discarded temporarily for purposes of reusing the scalpel. Conventionally, it is almost always the case that a surgeon is required to take his or her eyes away from the surgical field by turning his or her head towards a nurse in seeking to discard a scalpel or towards a nurse later seeking to hand the surgeon a previously discarded scalpel. This requires the surgeon to refocus again on the surgical field and can be an impediment to the surgeon's work by virtue of the surgeon's concentration having been broken. However, resort to the use of the instant invention obviates virtually totally this problem. Utilization of the instant invention enables a surgical nurse to lift a discarded scalpel from the wall of the invention by the handle only and readily place the handle within the compressible, elastic halves of the slit leg of the anterior portion of the rectilinear cap of the invention where it will rest handle out and firmly held and from where it can be very easily be withdrawn by the surgeon when needed without having to take his or her eyes from the surgical field.

Respectfully submitted, the above-noted features of the instant invention, that permit ready discarding of a scalpel without a surgeon's having to ake his or her eyes fromt he surgical field when doing so and that concomitantly obviate blade handling by a nurse and that later permit ready withdrawal therefrom of a re-readied scalpel by a surgeon without the surgeon's having to turn his or her head to do so and in so doing thereby obviate any need for the surgeon to ever take his or her eyes away from his or her surgical field serve to render the instant invention truly new, useful, unquestionably unique and veritably revolutionary in the art relating to such devices.

A DESCRIPTION OF THE DRAWINGS

Figure 2:
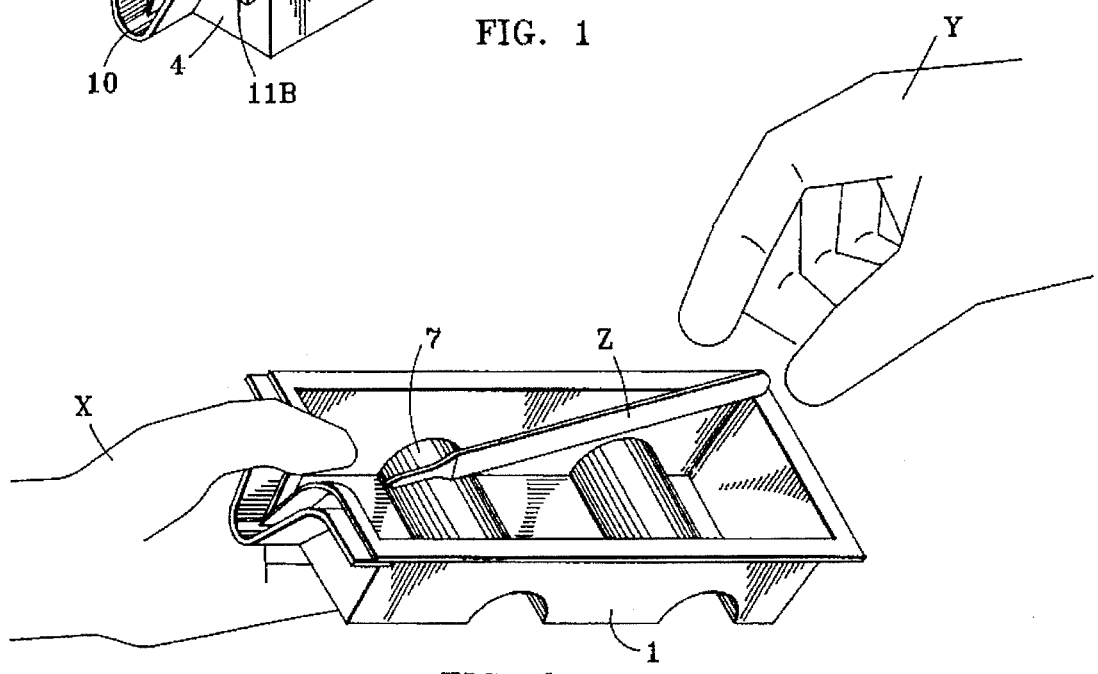
Figure 3:
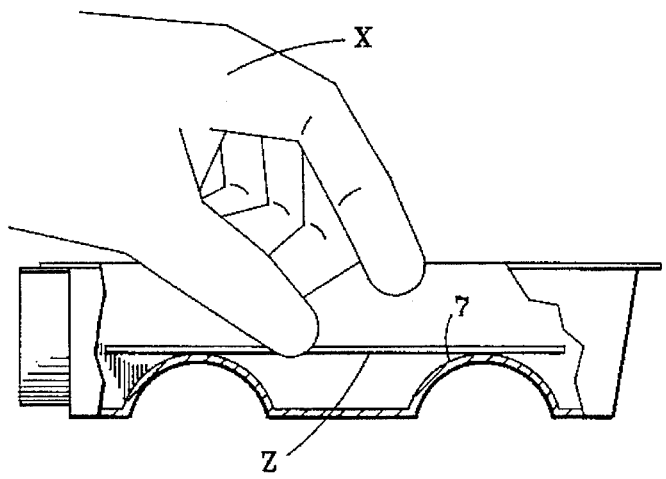
Figure 4:
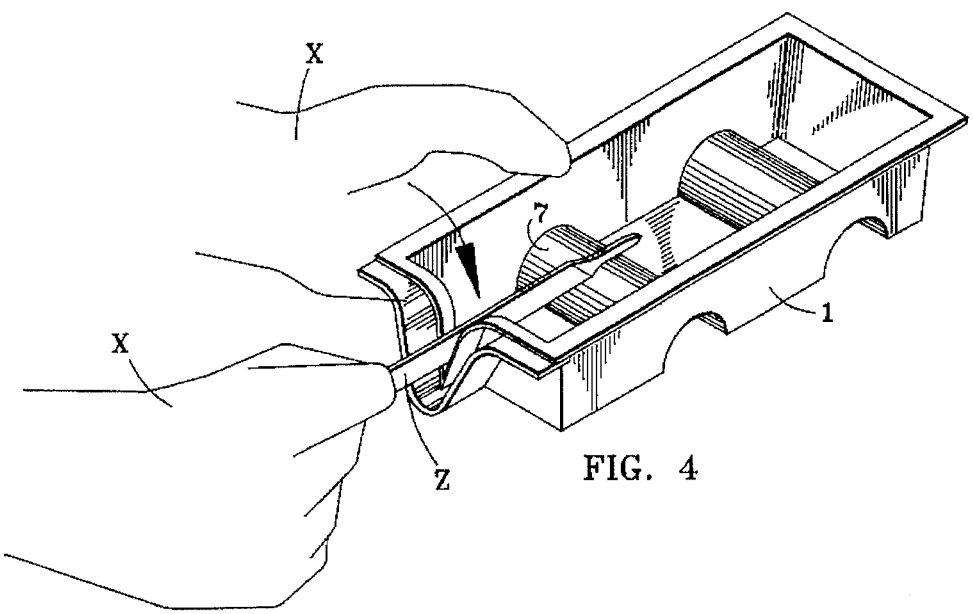
Figure 5:
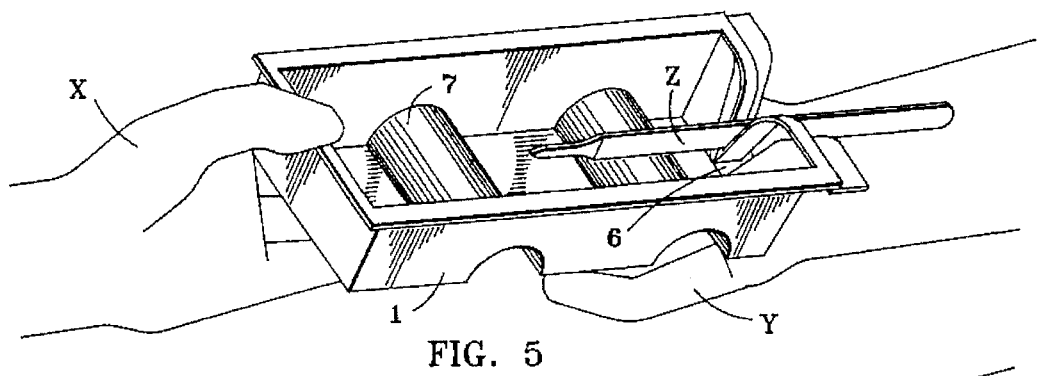
Figure 6:
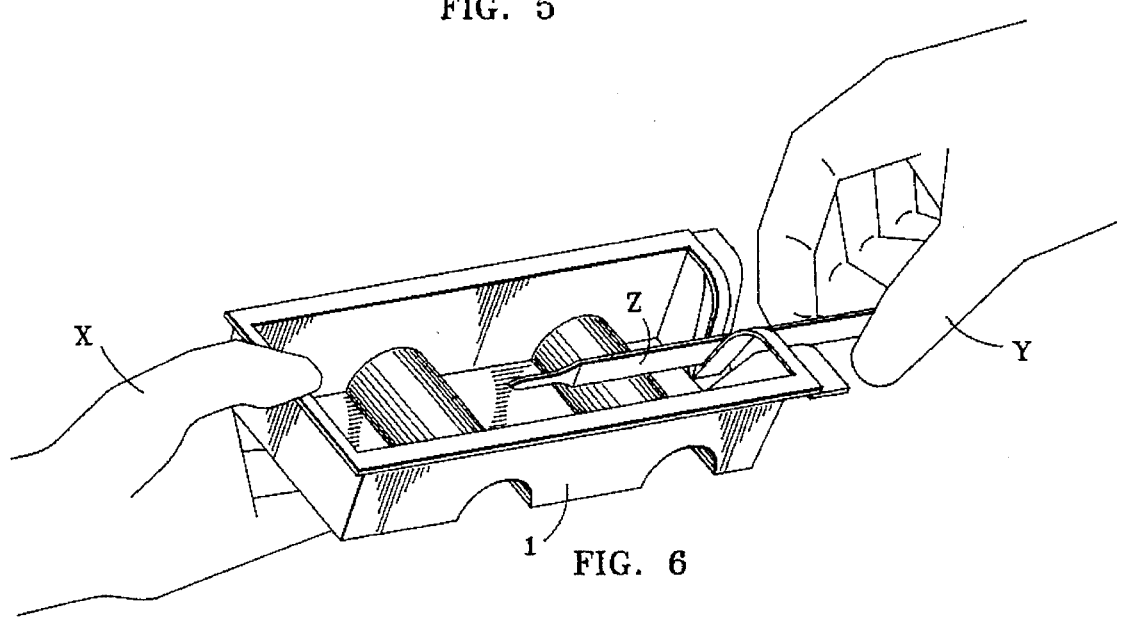
Figure 7:
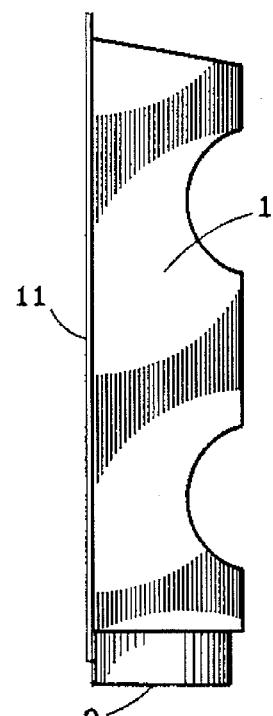
Figure 8:
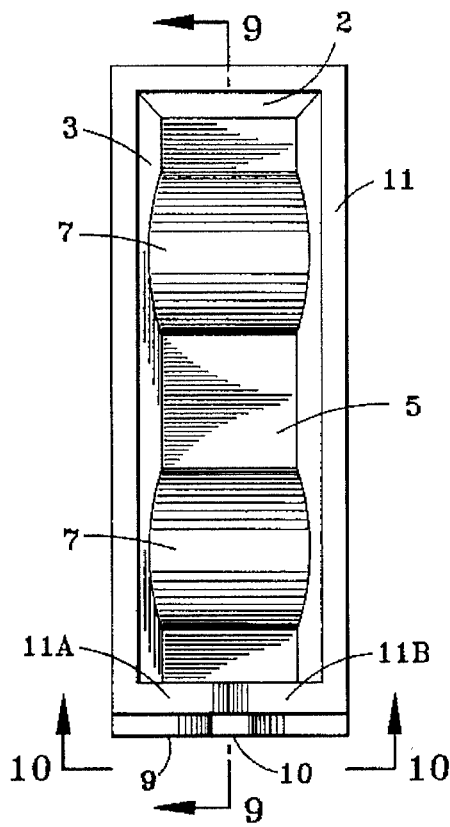
Figure 9:
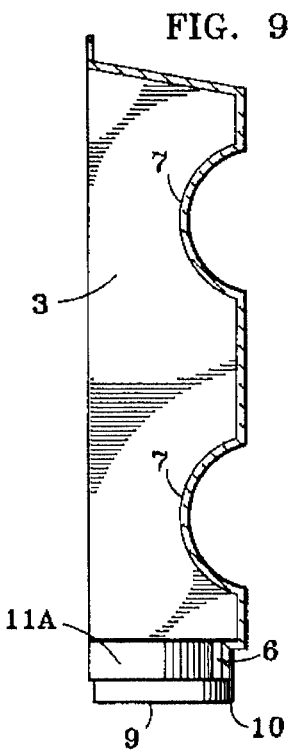
Figure 10:
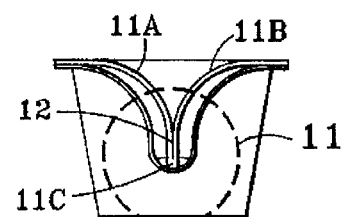
Figure 11:
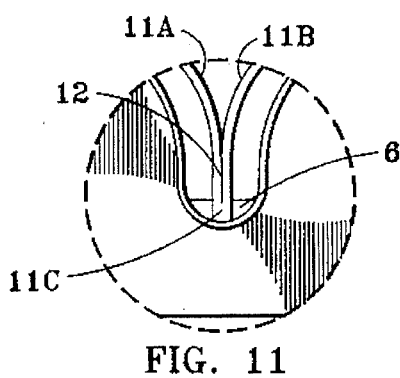
Figure 11A:
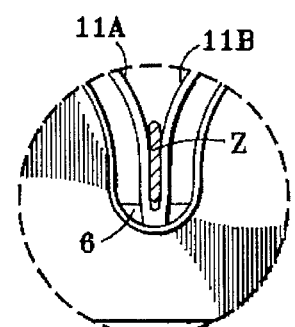

1. FIG. 1 is a perspective view of the instant invention.
2. FIG. 2 is a view of the instant invention shown receiving a scalpel being discarded by the hand of a surgeon.
3. FIG. 3 is a view showing a discarded scalpel being repositioned by the hand of a nurse within the well of the invention.
4. FIG. 4 is a view showing the discarded scalpel seen in FIG. 3 being positioned by the hand of a nurse for reuse by a surgeon.
5. FIG. 5 is a view of the instant invention holding a readied scalpel being handed by the hand of a nurse to a surgeon.
6. FIG. 6 is a view of the hand of the surgeon of FIG. 5 undertaking to withdraw the scalpel held by the instant invention for reuse.
7. FIG. 7 is a top view of the instant invention.
8. FIG. 8 is a right lateral view of the instant invention.
9. FIG. 9 is a longitudinal cross-sectional view of the instant invention.
10. FIG. 10 is an isolated frontal view of the compressible, elastic anterior portion of the rectilinear cap of the invention.
11. FIG. 11 is a close-up isolated frontal view of the compressible, elastic anterior portion of the rectilinear cap of the instant invention.
11A. FIG. 11A is an isolated frontal view of the compressible, elastic anterior of the rectilinear cap of the instant invention holding a scalpel readied for reuse.

A DESCRIPTION OF THE PREFERRED EMBODIMENTS

FIG. 1 is a perspective view of the intact instant invention. It is a recessed tray unit with a floor 5 that is medially level and with an anteriorly level lie at and about an anterior end of floor 5 as well as with a posteriorly level lie at and about a posterior end of floor 5. There is an outwardly inclined anterior sidewall 4 joined at its base to the whole of the anterior end of floor 5 and joined at a first anterior lateral edge to an anterior edge of an outwardly inclined first lateral side wall 1 and at a second anterior lateral edge to an anterior edge of an outwardly inclined second lateral sidewall 3. There is an outwardly inclined posterior sidewall 2 joined at its base to the whole of the posterior end of floor 5 and joined at a first posterior lateral edge to a posterior edge of outwardly inclined first lateral sidewall 1 and at a second posterior lateral edge to a posterior edge of outwardly inclined second lateral sidewall 3. First lateral sidewall 1 is also joined basally to the first lateral edge of floor 5 and second lateral sidewall 3 is also joined basally to the second lateral edge of floor 5. The outward angles of inclination of sidewalls 1, 2, 3 and 4 are all equal to one another. Within the surface of floor 5, there is a first convex rounded elevation 7 that is everywhere located closer to floor 5's anterior end and than to floor 5's posterior end. Elevation 7 extends from and out of the surface of first lateral sidewall 1 and into the surface of second lateral sidewall 3. Within the surface of floor 5, there is also a second convex rounded elevation 8 that is everywhere located closer to floor 5's posterior end than to floor 5's anterior end. Elevation 8 extends from and out of the surface of first lateral sidewall 1 into the surface of second lateral sidewall 3. The level medial portion of floor 5 lies between elevation 7 and elevation 8. the long antero-posterior central axis of floor 5 has length greater than the length of a surgical scalpel. The above-noted features of the instant invention enable a surgeon Y to readily toss as per FIG. 2 a scalpel Z which he or she seeks to discard during the course of surgery into the well of the instant invention such that scalpel Z will be assured of falling flat into the well and, moreover, atop elevation 7 and 8. Surgeon Y can do so without any need to remove his or her eyes from the surgical field with which he or she is then involved. A nurse X can then readily pick up, as per FIG. 3, scalpel Z by the handle for purposes of repositioning scalpel Z for eventual reuse during surgery as per FIG. 4. As matters currently stand during the course of surgery, a surgeon Y seeking to discard a scalpel Z needs to hand it to a nurse X, and, in doing so, the risk of cutting the fingers or hand of nurse X with the bloody blade of a discarded scalpel Z and the concomitant risk of nurse X's contracting hepatitis or even worse perhaps AIDS as a result of having come in contact with the possibly contaminated blood of a patient is everpresent. However, as can be noted with resort to FIGS. 2,3 and 4 above, discarding of a scalpel Z and its repositioning for reuse by a nurse X during surgery is able to be accomplished with the aid of the instant invention without loss of efficiency and most importantly without risk of cuts or concomitant infection. The repositioning for reuse just noted replaces the need for a nurse X's without the aid of the instant invention having to hand bloody scalpel Z back to surgeon Y blade first and having to risk being cut as it is taken by surgeon Y from nurse X's hand.

Repositioning for reuse is made possible by virtue of the presence of a notch 6 seen in FIG. 5 which is centrally located in anterior sidewall 4 which notch 6 serves to receive the lowest point of the anterior portion of hollow rectilinear cap 11 seen in FIG. 7 which fits atop the top edges of sidewalls 1, 2, 3 and 4 of the instant invention. The lowest portion of notch 6 consists of a locus of continuous first points running antero-posterior each of which is equidistant from sidewall 1 and sidewall 3. Notch 6 is wide enough to receive a scalpel resting on its bottom side. The lowest point of the anterior portion of rectilinear cap 11 as seen in FIG. 11 is the bottom of a leg 11c of a Y shaped piece of compressibly elastic material. As can be seen with resort to FIGS. 9, 11 and 11A. This anterior portion of rectilinear cap 11 which anterior portion is also endwise contiguous with the anteriormost portions of the lateral sides of rectilinear cap 11 curves bilaterally inward and downward in a symmetrical fashion such that part 11A and part 11B of this anterior portion are equal in length and curve each in a gently convex manner to a termination point in the base of leg 11C as seen in FIG. 11, the long vertical central axis of leg 11C is comprised of a continuum of points each of which is equidistant from lateral sidewall 1 and lateral sidewall 3. This anterior portion throughout leg 11C and throughout part 11A and part 11B in the vicinity of leg 11C is made up of a compressibly elastic material. A slit 12 is cut into leg 11C along its long vertical central axis as is seen in FIG. 11 down to a point just above its base. Slit 12 and the compressible elasticity of and about leg 11C enable a nurse X to dependably and firmly reposition for reuse within the midsection of leg 11C a previously discarded scalpel 5 as per FIG. 4 and as per FIG. 11A, all as noted above. The convexity of parts 11A and 11B as can be noted with resort to FIG. 10 readily facilitates a surgeon Y's simply tactally running his or her hand quickly down to the locus of the handle of scalpel Z held firmly in place by virtue of the compressible elasticity of and about leg 11C in an effort to grasp it without any need to lose valuable time and/or concentration on the surgical task at hand such as might otherwise happen in the event of a need to remove his or her eyes from the surgical field absent the availability of the instant invention to hopefully safely grasp a scalpel Z being handed to him taking care all the while so as not to cut the hand of the nurse X handing it over. Removal of one's eyes from a surgical field and then refocusing them thereupon and therein can cause the loss of valuable time and concentration during surgery, since, for example, it's often the case that a primary surgical light source on the surgeon forehead needs likewise to be properly redirected. There is also another component of the instant invention that needs to be discussed, and that is its anteriorly positioned horizontally outward extending component 9 as seen also in FIG. 1. Component 9 is shaped in the form of a gently u-shaped notch, the lowest site within which is a centrally positioned locus 10 of a continuum of second points all running antero-posterior in a line parallel to the line containing all of the first points of notch 6. The long central axis of leg 11C and locus 10 and all of the first points of notch 6 are coplanar and component 9 serves to more readily ensure that a scalpel Z repositioned handlewise within slit 12 of leg 11C as seen in FIG. 11A will stay put and not perchance fall downward handle first should the instant invention be accidentally jostled during surgery while holding a repositioned scalpel Z. FIG. 7 is a top view of the instant invention. FIG. 8 is a lateral view of the instant invention. FIG. 9 is a cross-sectional lateral view of the instant invention. FIG. 10 is frontal view of component 9 and the anterior portion of rectilinear cap 11 of the instant invention.

In closing, respectfully submitted, in view of the foregoing, the instant invention protecting against cuts and possibly infection as it does while enabling a surgeon Y's eyes to stay on the surgical field when discarding or grasping a scalpel Z is truly a revolutionary advance in the art as respects manufactured surgical instrumentalities.

What is claimed is:

1. A surgical scalpel cradle comprising:
   a. a recessed tray unit with a floor medially planar and anteriorly planar at and about an anterior end of said floor and posteriorly planar at and about a posterior end of said floor, with an outwardly inclined anterior sidewall joined at its base to the whole of said anterior end of said floor and joined at a first lateral edge to an anterior edge of an outwardly inclined first lateral sidewall also wholly joined to a first lateral end of said floor with said anterior sidewall also joined at a second lateral edge to an anterior edge of an outwardly inclined second lateral sidewall also wholly joined to a second lateral end of said floor and an outwardly inclined posterior sidewall joined to the said posterior end of said floor and joined to a posterior edge of said first lateral sidewall and joined to a posterior edge of said second lateral sidewall;
   b. said first lateral sidewall outwardly being inclined with an angle of inclination with respect to said medially planar portion of said floor and said anteriorly planar portion of said floor at and about said floor's said anterior end and said posteriorly planar portion of said floor at and about said floor's said posterior end and having an absolute numerical value equal to the absolute numerical value of the said outwardly inclined posterior sidewall's angle of inclination;
   c. said second lateral sidewall outwardly inclined with an angle of inclination with respect to said medially planar portion of said floor and said anteriorly planar portion of said floor at and about said floor's said anterior end and said posterior planar portion of said floor at and about said floor's said posterior end and having an absolute numerical value equal to the absolute numerical value of the said outwardly inclined posterior sidewall's angle of inclination;
   d. said anterior sidewall outwardly inclined with an angle of inclination with respect to said medially planar portion of said floor and said anteriorly planar portion of said floor at and about said floor's said anterior end and said posteriorly planar portion of said floor at and about said floor's said posterior end and having an absolute numerical value equal to the absolute numerical value of the said outwardly inclined posterior sidewall's angle of inclination;
   e. a first convex rounded elevation in the surface of said floor everywhere located closer to said floor's anterior end than to said floor's said posterior end and extending from and out of the surface of said first lateral sidewall to and into the surface of said second lateral sidewall;
   f. a second convex rounded elevation in the surface of said floor everywhere located closer to said floor's said posterior end than to said floor's said anterior end and extending from and out of the surface of said first lateral sidewall to and into the surface of said second lateral sidewall;
   g. said floor's long antero-posterior central axis having length in excess of the length of a surgical scalpel;
   h. the distance between said first convex rounded elevation and said second convex rounded elevation being less than the length of a surgical scalpel;
   i. said anterior sidewall having cut into it a notch amenable to receipt of a handle of a surgical scalpel resting on the bottom side of said handle with the lowest portion of said notch constituting the locus of a continuum of first points all running straight front to back with all of said first points each equidistant from said first lateral sidewall and said second lateral sidewall;
   j. a hollow rectilinear cap affixed posteriorly to the top edge of said posterior sidewall, affixed laterally to the top edge of said first lateral sidewall and to the top edge of said second lateral sidewall, the anterior portion of which said cap is affixed to a right top edge of said anterior sidewall and to a left top edge of said anterior sidewall and which said anterior portion is continuously one piece of material that symmetrically curves bilaterally inward and downward from each of said anterior portion's ends to form a shape in the form of a letter Y with the two arms of said shape in the form of a letter Y being equally convex in curvature and terminating each in the leg of said shape in the form of a letter Y, the long vertical central axis of said leg of said shape in the form of a letter Y being equidistant from said first lateral sidewall and from second lateral sidewall with the lowest point of said leg being the lowest point of said anterior portion;

k. said leg of said shape in the form a letter Y having a vertical slit cut into it along the lie of said leg's long vertical central axis down to a point just above the lowest point of said leg with said slit being coplanar with all of said first points and all of said second points;

l. said anterior portion of said rectilinear cap being compressibly elastic within the vicinity of and throughout the whole of said leg of said shape in the form of a letter Y.

2. A surgical scalpel cradle, comprising:

a. a recessed tray unit with a floor medially planar and anteriorly planar at and about an anterior end of said floor and posteriorly planar at and about a posterior end of said floor, with an outwardly inclined anterior sidewall joined along its base to the whole of said anterior end of said floor and joined at a first lateral edge to an anterior edge of an outwardly inclined first lateral sidewall also wholly joined along its base to a first lateral end of said floor with said anterior sidewall also joined at a second lateral edge to an anterior edge of an outwardly inclined second lateral sidewall also wholly joined to a second lateral end of said floor and with an outwardly inclined posterior sidewall joined to the said posterior end of said floor and joined to a posterior edge of said first lateral sidewall and joined to a posterior edge of said second lateral sidewall;

b. said first lateral sidewall outwardly inclined with an angle of inclination with respect to the said medially level lie of said floor and said anteriorly level lie of said floor at and about said floor's said anterior end and said posteriorly level lie of said floor at and about said floor's said posterior end and having an absolute numerical value equal to the absolute numerical value of the said outwardly inclined posterior sidewall's angle of inclination;

c. said second lateral sidewall outwardly inclined with an angle of inclination with respect to the said medially level lie of said floor and said anteriorly level lie of said floor at and about said floor's said anterior end and said posterior level lie of said floor at and about said floor's said posterior end and having an absolute numerical value equal to the absolute numerical value of the said outwardly inclined posterior sidewall's angle of inclination;

d. said anterior sidewall outwardly inclined with an angle of inclination with respect to the said medially level lie of said floor and said anteriorly level lie of said floor at and about said floor's said anterior end and said posteriorly level lie of said floor at and about said floor's said posterior end and having an absolute numerical value equal to the absolute numerical value of the said outwardly inclined posterior sidewall's angle of inclination;

e. a first convex rounded elevation in the surface of said floor everywhere located closer to said floor's anterior end than to said floor's said posterior end and extending from and out of the surface of said first lateral sidewall to and into the surface of said second lateral side;

f. a second convex rounded elevation in the surface of said floor everywhere located closer to said floor's said posterior end than to said floor's said anterior end and extending from and out of the surface of said first lateral side wall to and into the surface of said second lateral sidewall;

g. said floor's long antero-posterior central axis having length in excess of the length of a surgical scalpel;

h. the distance between said first convex rounded elevation and said second convex rounded elevation being less than the length of a surgical scalpel;

i. said anterior sidewall having cut into it a notch amenable to receipt of a handle of a surgical scalpel resting on the bottom side of said handle with the lowest portion of said notch constituting the locus of a continuum of first points all running straight front to back with all of said first points each equidistant from said first lateral sidewall and said second lateral sidewall;

j. a hollow rectilinear cap affixed posteriorly to the top edge of said posterior sidewall, affixed laterally to the top edge of said first lateral sidewall and to the top edge of said second lateral sidewall, the anterior portion of which said cap is affixed to a right top edge of said anterior sidewall and to a left top edge of said anterior sidewall and which said anterior portion is continuously one piece of material that symmetrically curves bilaterally inward and downward from each of said anterior portion's ends to form a shape in the form of a letter Y with the two arms of said shape in the form of a letter Y being equally convex in curvature and terminating each in the leg of said shape in the form of a letter Y, the long vertical central axis of said leg of said shape in the form of a letter Y being equidistant from said first lateral sidewall and from second lateral sidewall with the lowest point of said leg being the lowest point of said anterior portion;

k. said leg of said shape in the form a letter Y having a vertical slit cut into it along the lie of the long vertical central axis of said leg down to a point just above the lowest point of said leg with said slit being coplanar with all of said first points and all of said second points;

l. said anterior portion of said rectilinear cap being compressibly elastic within the vicinity of and throughout the whole of said leg of said shape in the form of a letter Y;

m. a horizontally, outwardly directed extension component affixed to said anterior sidewall and in the shape a u-shaped notch with the lowest portion of said u-shaped notch constituting the locus of a continuum of second points all running straight front to back with all of said second points in a line parallel to the line containing all of said first points.

\* \* \* \* \*